Figure 1:
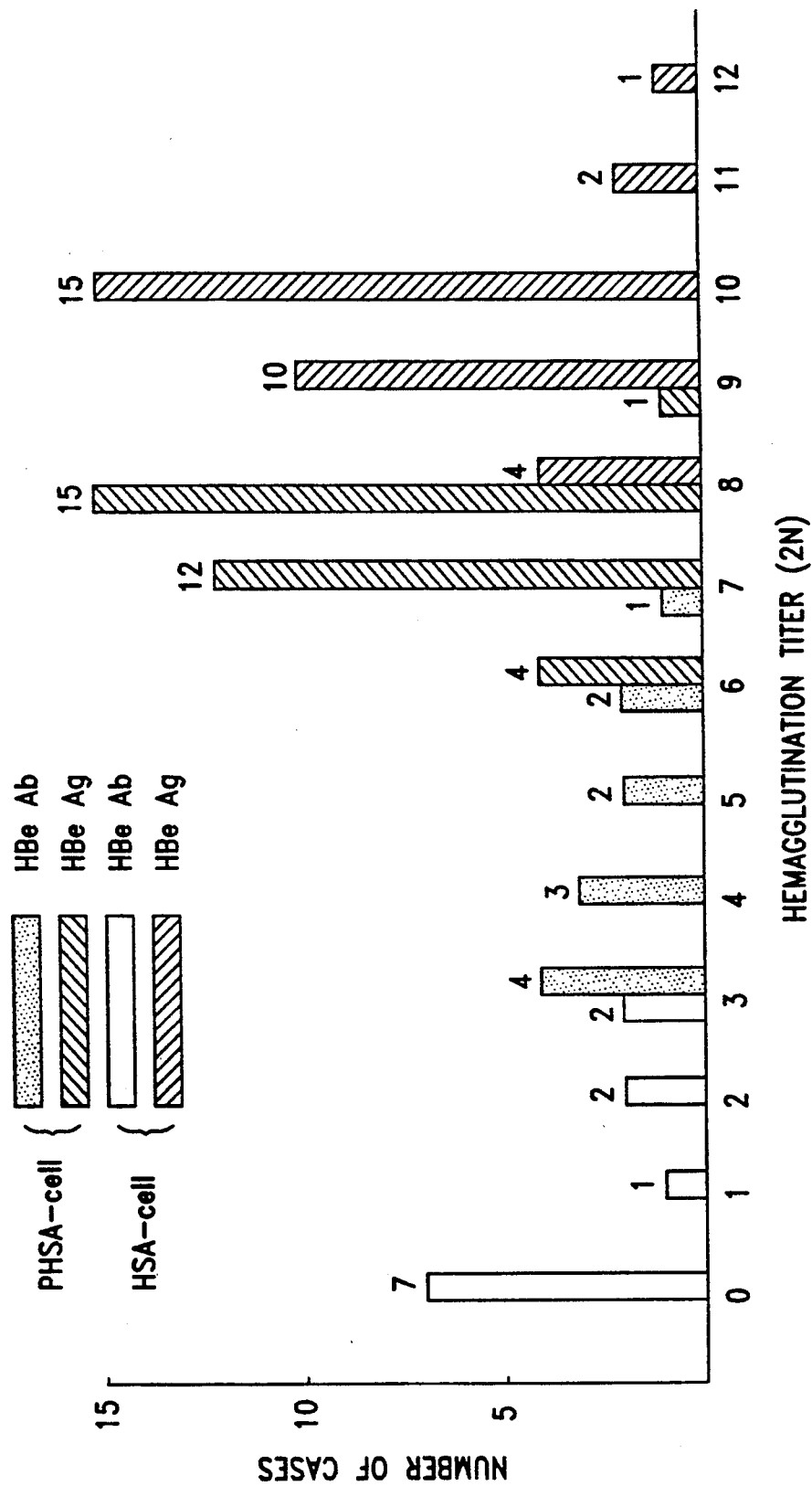

United States Patent [19]

Ko et al.

[11] Patent Number: 5,316,936
[45] Date of Patent: May 31, 1994

[54] METHOD FOR PREPARATION OF HUMAN SERUM ALBUMIN-SENSITIZED SHEEP ERYTHROCYTES (HSA-CELL) FOR DETECTION OF PRE-S2 ANTIGEN

[76] Inventors: Jin-Nam Ko, Pipa 2, don 30 ban, Moranbong Guyok; On-Sun Pak, Kansong dong 57 ban, Pyongchon Gyuok, both of Pyongyang, Rep. of Korea

[21] Appl. No.: 752,850

[22] Filed: Aug. 30, 1991

[30] Foreign Application Priority Data

Sep. 1, 1990 [KP] D.P.R. of Korea ............... 90-2439

[51] Int. Cl.$^5$ .............................................. A61K 35/18
[52] U.S. Cl. ................................ 435/240.2; 424/533; 436/521; 436/820
[58] Field of Search ............... 424/533; 435/240.2; 436/521, 820

[56] References Cited

PUBLICATIONS

Savelkoul et al., J. Immunol Methods 111 (1):31–38 (1988) Abstract BA86:69875.
Basmadzhyan et al., Zh Eksp Klin Med 19(3):56–58 (1979) Abstract BA71:31277.
Derechiskaya et al., Lab Delo 0(12):25–29 (1989) Abstract BA90:40107.
A. Machida, et al., "A Hepatitis B Surface Antigen Polypeptide (P32) With the Receptor for Polymerized Human as Well as Chimpanzee Albumins", Gastroenterology, vol. 85, No. 2, 1983.
Y. Itoh, et al., "A Synthetic Peptide Vaccine Involving the Product of the Pre-S(s) Region of Hepatitis B Virus DNA: Protective Efficacy in Chimpanzees", Proc. Natl. Acad. Sci. U.S.A., vol. 83, 1986.
P. Tiollais, et al., "Biology of Hepatitis B Virus", Science, vol. 213, 1981.
M. Imai, et al., "A Receptor for Polymerized Human and Chimpanzee Albumins on Hepatitis B Virus Particles Co-occuring with HBeAg", Gastroenterology, vol. 76, No. 2, 1979.
H. Okamoto, et al., "Hemagglutination Assay of Polypeptide Coded by the Pre-S Region of Hepatitis B Virus DNA with Monoclonal Antibody: Correlation of Pre-S Polypeptide with the Receptor for Polymerized Human Serum Albumin in Serums Containing Hepatitis B Antigens", The Journal of Immunology, vol. 134, No. 2, 1985.

Primary Examiner—Douglas W. Robinson
Assistant Examiner—Jean C. Witz
Attorney, Agent, or Firm—Kenyon & Kenyon

[57] ABSTRACT

A method for preparation in a large quantity of human serum albumin-sensitized sheep erythrocytes is described. The sensitized cells are useful for detecting Hepatitis B virus pre-S$_2$ antigen. The method uses human serum albumin sensitized glutaraldehyde-fixed, sheep erythrocytes in the presence of chromium chloride.

5 Claims, 1 Drawing Sheet

METHOD FOR PREPARATION OF HUMAN SERUM ALBUMIN-SENSITIZED SHEEP ERYTHROCYTES (HSA-CELL) FOR DETECTION OF PRE-S2 ANTIGEN

Pre-S$_2$ Antigen protein can express polymerized human serum albumin binding activity (PHSA-BA). (A. Machida et al. *A polypeptide containing 55 amino acid residues coded by the pre-S region of hepatitis B virus deoxyribonucleic acid bears the receptor for polymerized human as well as chimpanzee albumins*, 86 Gastroenterology 910 (1984)). Furthermore, the epidemiological and clinical significance of this protein has been clarified. (T. Matsuhashi et al. *Reactants to human serum albumin-coated red blood cells found in Au(1)-positive sera*, 12 Jpn. J. Exp. Med. 183 (1972); M. Imai et al. *A receptor for polymerized human and chimpanzee albumins on hepatitis B virus particles co-occurring with HBsAg*. 76 Gastroenterology 242 (1979); I. Tsu et al. *Detection of serum albumin receptor in hepatitis enterology*, 17 Jap. 585 (1982); A. R. Neurath et al. *Location and chemical synthesis of a pre-S gen coded immuno-dominant epitope of hepatitis B virus*, 224 Science 392 (1984); Milich et al. *Enhanced immunogenicity of the pre-S region of hepatitis B surface antigen*, 228 Science 1195 (1985)). However, all immuno assays developed so far for this protein use molecularizing of human serum albumin in a polymerized form and binding with various sorbents.

We discovered that HBV-associated polymerized human serum albumin receptor also binds non-polymerized human serum albumin. Using affinity chromatography we purified the HBs Ag protein containing pre-S$_2$ polymerized with human serum albumin binding activity from the HBV envelope proteins. We then used this complex to prepare our human serum albumin-sensitized erythrocytes (HSA-cells).

Human serum albumin (Sigma, U.S.A. Lot 127F-9307, or albumin preparation produced according to instruction No. 1320 issued by Ministry of Public Health of DPRK) or the serum of healthy adult is diluted in saline to a protein content in the range of 312–1250 $\mu$g/ml.

We added this HSA protein solution at the ratio of 3:1 to 50% erythrocytes fixed by 2,5% glutaraldehyde by a known method. (K. J. Nam et al., *Method of preparation of high sensitivity speed immuno serum diagnosis preparation for detection of HBs antigen*, DPRK Invention certificate No. 25377 (1990)). Immediately thereafter, we added a 0.5–3% solution of chromium chloride to the HSA protein-erythrocyte solution at the ratio of 3:1:1.

After a 15–20 minute incubation at room temperature, we washed the cells twice with saline. Next we washed the cells once with a saline solution containing 1% normal sheep serum. We then suspended the cells in the 1% normal sheep saline at a 0.8–1% cell concentration, thus obtaining our HSA-cells.

EXAMPLE 1

We dissolved HSA (Sigma, U.S.A. Lot 127F-9307) in saline at several concentrations between 312.5–1250 $\mu$g/ml, including at 625 $\mu$/ml. To 30 ml of this solution, we added 10 ml of 50% fixed sheep red blood cells (SRBC) and 10 ml of 1% chromium chloride in saline. After a 20 minute incubation at room temperature, we washed HSA-SRBC combination twice with saline. Finally, we suspended the combination in 625 ml of saline containing 1% of normal sheep serum. This procedure produced a quantity of HSA-cells sufficient to screen 25,000 cases.

EXAMPLE 2

We diluted a healthy adult's serum in saline to a protein content of between 800–1200 $\mu$g/ml. To 60 ml of this serum solution, we added 20 ml of 50% SRBC and 20 ml of 1.5% chromium chloride solution. We then incubated the admixture at room temperature for 15 minutes. Thereafter, we washed and suspended the admixture as described in Example 1. This procedure produced 1250 ml of a HSA-cell combination which was sufficient to screen 50,000 cases. We measured the sensitivity, specificity and stability of our HSA-cell combination as follows:

(A) Sensitivity

We prepared polymerized human serum albumin. sensitized sheep erythrocytes (PHSA-cell) by a known method. (M. Imai et al. *A receptor of polymerized human and chimpanzee albumins on hepatitis B virus particles co-occurring with HBeAg*, 76 Gastroenterology 242 (1979)). We compared the sensitivity of the PHSA-cells to that of our HSA-cells. The results are shown in table 1. As is seen in table 1, the sensitivity of our HSA-cells was 4 times higher than that of the PHSA-cells.

TABLE 1

| | Final agglutination titer* on human serum albumin binding activity | |
|---|---|---|
| Specimen No. | Polymerized human serum albumin-sensitized erythrocytes (PHSA-cell) | Human serum albumin-sensitized erythrocytes (HSA-cell) |
| 1 | 1024 | 1096 |
| 2 | 512 | 2048 |
| 3 | 512 | 2048 |
| 4 | 128 | 1024 |

*Final agglutination titer was expressed in maximum dilution number in which more than 2 degree agglutination occurred on the microtiter plate (U) by the micro titration method (Judgement after 1 hour at 37° C. for incubation).

(B) Specificity

We conducted a Hemagglutination assay on the serum from 96 HBs Ag - negative healthy adults. Non specific agglutination occurred in serum dilutions 1:8 for 43.8% cases using the PHSA-cells. The literature reports similar levels of non-specific agglutination, i.e.. 35.9% cases. In contrast, using our HSA-cells, we did not observe any non-specific agglutination at that dilution (table 2).

TABLE 2

| | Non-specific agglutination ratio among HBs Ag-negative test materials (96 cases) | | | | | |
|---|---|---|---|---|---|---|
| | Cell | | | | | |
| | HSA-Cell | | | PHSA-Cell | | |
| Index | 1:2 | 1:4 | 1:8 | 1:2 | 1:4 | 1:8 |
| Number of cases of non-specific agglutination | 8 | 3 | 0 | 81 | 55 | 42 |
| Non-specific agglutination ratio (%) | 8.3 | 3.1 | | 84.3 | 57.3 | 43.8 |

Also, as shown in FIG. 1, we found that our HSA-cells were more specific than the PHSA-cells were.

(3) Stability

Table 3 shows that the sensitivity of the PHSA-cells declined to one eighth 3 days after their preparation. Furthermore, the PHSA-cells lost nearly all of their agglutinating capacity after 30 days storage at 4°–10° C.

In contrast, our HSA-cells maintained their effective sensitivity for more than 6 months at room temperature, and for 30 days at 37° C.

TABLE 3

| | | Stability with preservation condition and period (day). | | | | | | | | | |
|---|---|---|---|---|---|---|---|---|---|---|---|
| | | | | | | Preservation period (day) | | | | | |
| Cell | | Immed. after preparation | 3 | 5 | 30 | 60 | 90 | 120 | 150 | 180 | 210 |
| PHSA-Cell | 4–10° C. | 512 | 64 | 64 | 16–32 | | | | | | |
| | Room Temp. | 512 | 64 | 64 | 8–16 | | | | | | |
| | 37° C. | 512 | 32 | 8–16 | — | | | | | | |
| HSA-Cell | 4–10° C. | 2048 | 1024 | 1024 | 1024 | 1024 | 1024 | 1024 | 1024 | 1024 | under observ. |
| | Room Temp. | 2048 | 1024 | 1024 | 1024 | 512 | 512 | 512 | 512 | 512 | under observ. |
| | 37° C. | 2048 | 1024 | 1024 | 512 | under observ. | | | | | |

We claim:

1. A method for preparing human serum albumin-sensitized sheep erythrocytes for detecting pre-S₂ antigen comprising:
   (a) fixing sheep erythrocytes;
   (b) adding human serum albumin in a saline solution to said fixed sheep erythrocytes;
   (c) adding a 0.5 to 3% solution of chromium chloride to said fixed sheep erythrocytes and human serum albumin combination, said sheep erythrocytes, human serum albumin and chromium chloride are combined in the ratio of 3:1:1.

2. The method according to claim 1 in which said human serum albumin is purified human serum albumin and is present at a concentration of between 312.5 and 1250 μg/ml.

3. The method according to claim 1 in which said human serum albumin is unpurified human serum albumin and is present at a concentration of between 800 and 1250 μg/ml.

4. The method according to claim 1 in which said fixing step comprises the use of a glutaraldehyde solution.

5. The method according to claim 4 in which said glutaraldehyde solution has a concentration of about 2.5%.

* * * * *

UNITED STATES PATENT AND TRADEMARK OFFICE
CERTIFICATE OF CORRECTION

PATENT NO. : 5,316,936
DATED : May 31, 1994
INVENTOR(S) : Ko et al.

It is certified that error appears in the above-indentified patent and that said Letters Patent is hereby corrected as shown below:

On the Title page, item [76], change "Rep. of Korea" to --D.P.R. of Korea--.

Column 2, line 19, delete the period at the end of the line and insert a hyphen.

Signed and Sealed this

Fourth Day of October, 1994

Attest:

BRUCE LEHMAN

*Attesting Officer*   *Commissioner of Patents and Trademarks*